United States Patent [19]

Caspar et al.

[11] Patent Number: 4,616,635
[45] Date of Patent: Oct. 14, 1986

[54] SURGICAL INSTRUMENT FOR THE SPLAYING OF WOUND EDGES

[75] Inventors: Wolfhard Caspar, Bad Homburg; Theodor Lutze, Balgheim; Theodor Schwarz, Tuttlingen, all of Fed. Rep. of Germany

[73] Assignee: Aesculap-Werke Aktiengesellschaft, Tuttlingen, Fed. Rep. of Germany

[21] Appl. No.: 719,687

[22] Filed: Apr. 4, 1985

[30] Foreign Application Priority Data

Apr. 4, 1984 [DE] Fed. Rep. of Germany ....... 3412647
Mar. 19, 1985 [DE] Fed. Rep. of Germany ....... 3509787

[51] Int. Cl.⁴ ............................................. A61B 17/02
[52] U.S. Cl. .................................................... 128/20
[58] Field of Search .......................................... 128/20

[56] References Cited

U.S. PATENT DOCUMENTS 3,384,078  5/1968  Gauthier ................................ 128/20
4,116,232  9/1978  Rabban ................................. 128/20

FOREIGN PATENT DOCUMENTS 2272632  12/1975  France ................................. 128/20

Primary Examiner—William H. Grieb
Attorney, Agent, or Firm—Kenway & Jenney

[57] ABSTRACT

An instrument for the splaying of the edges of a wound which has at least one blade. The blade has a middle part, a rim projecting at right angles from the middle part, and a mount on which the middle part is held. The middle part has two parts movable against each other by an actuator comprising a turnable rod with a screw thread section.

11 Claims, 8 Drawing Figures

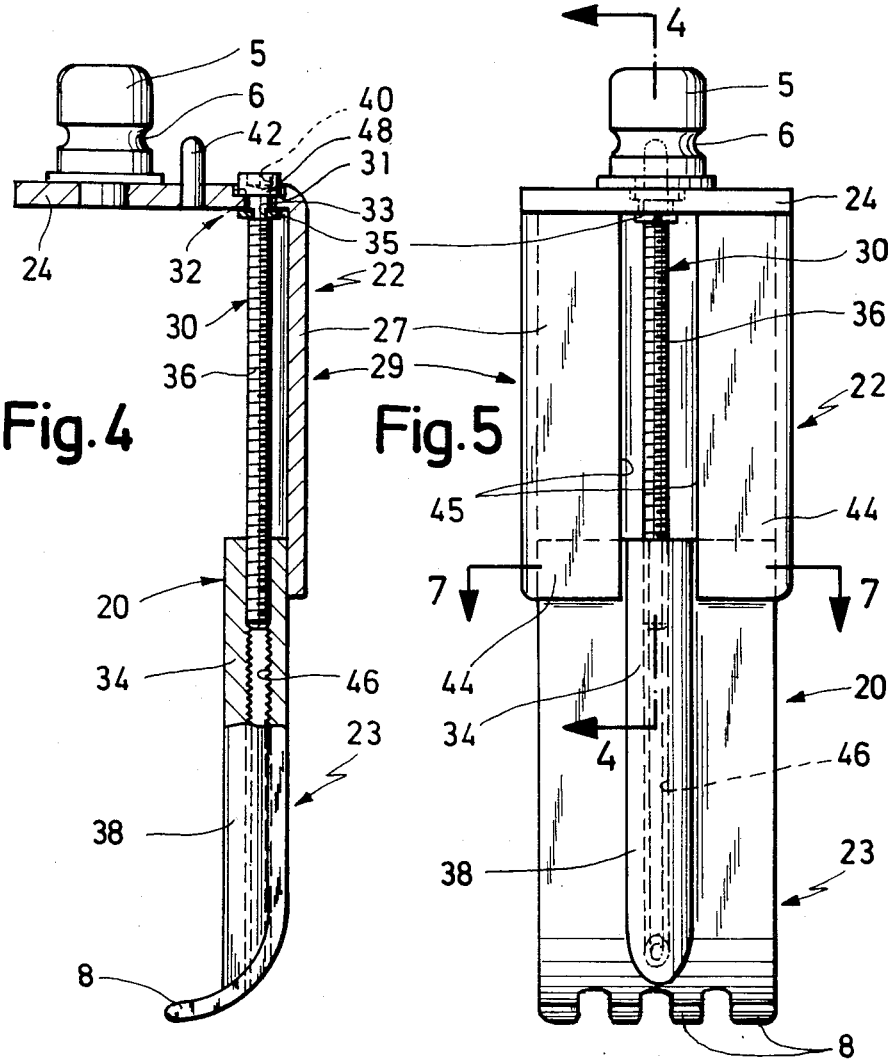

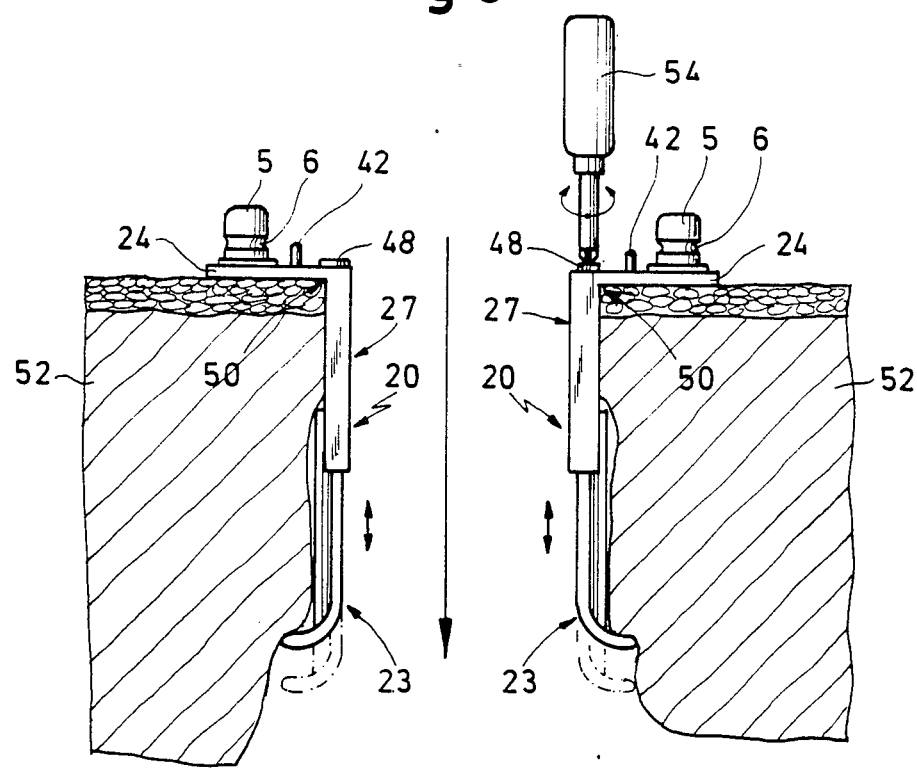

SURGICAL INSTRUMENT FOR THE SPLAYING OF WOUND EDGES

The invention concerns a surgical instrument for the splaying of wound edges with at least one blade for contact with the wound edges each of which has a blade-shaped middle part and a rim projecting approximately at right angles, and with a mount to which the blade is fastened to the end of the middle part lying opposite the projecting rim.

Such instruments with spade-shaped blades are used in order to splay the edges of wounds, for example in order to free the access to an area of operation. In such instruments the mount can carry only one blade and often two blades are fastened to the mount in different spacings from each other so that opposite wound edges are splayed.

A surgical instrument with one-piece blades is known from FR-PS No. 690 530. These are held on a mount in two adjustable directions perpendicular to one another. The first setting allows a splaying of the wound edges, the second allows an adjustment of the mount to the size of the body part to be operated which can then be encircled by the blade-carrying mount. A disadvantage in this construction is the unchangeable area of reach of the individual blades.

The length of the blades must differ according to the respective application. The length of the blades depends, for example, on the position of the operational area or on the thickness of the tissue layers to be held back. For this reason, such a surgical splaying instrument as a rule comprises a set of blades of different lengths which can be connected with the mount as required. This not only means a considerable expenditure in purchasing and storage, but in many cases one can only determine during the operation which blade size is required, so that the blades must be changed even during the operation. This is awkward and time-consuming.

It is the task of the invention to improve a surgical instrument of the generic type in such a way that it can be used with a single blade even with different strengths of the wound edge.

This task is solved by means of a surgical instrument of the above described type according to the invention in such a way that the middle part comprises two parts that are adjustable against each other, of which one is fastened to the mount and the one has the projecting rim, and that both parts can be fixed to each other in different relative positions so that different lengths of the middle part formed by both parts and thus different spacings of the projecting rim from the mount result. Through this design the effective length of the blade can be adjusted so that an adjustment to the respective circumstances is quickly possible, without the blade having to be changed.

It is of advantage if the two parts of the middle part lie against each other on a flat plane; this results in a secure movement of both parts to one another.

This design is even more improved if the the two parts of the middle part are arched diagonally to their adjustment direction.

A preferred design form provides for at least one longitudinal slit to be put into one of the two parts, and for at least one guide element fastened to the other part to project into the slit. Preferrably the guide element is adjustable in its spacing from the other part between a clamping setting in which the two parts are tightly pressed against each other, and a release setting in which the two parts are movable toward each other. By adjusting the guide element between the two settings the two parts can quickly be shifted against each other and then placed back in the desired relative setting, so that even during the operation an adjustment at any time to the space requirements is possible.

It is advantageous if the guide element is a locking screw screwed into the other part.

It is especially advantageous if two parallel longitudinal slits are placed in the one part and if two guide elements project into each longitudinal slit. One obtains in this way an especially exact guiding of the two parts against each other.

In an especially preferred design form of this invention an adjustment of the area of reach of the blade is still possible without problems if the instrument has already been set into the wound. This is made possible by the fact that the two parts of the middle part that are adjustable against each other are adjustable relatively to one another in the shift direction by means of an actuator, whereby the actuator is activated outside of the wound for the instrument set into the wound.

Possibilities for actuators are for example slide shafts that can be clamped tightly or a combination of tooth shaft and a pinion gear cogging with it. It is favorable if the actuator has a turnable rod with a screw thread section, a guide part with an inner screw thread complementary to the screw thread of the rod and an abutment, whereby the guide part and the abutment are set against different parts of the middle part and guide and hold the rod parallel to the adjustment direction. By means of a turning of the rod one can now exactly set the area of reach of the blade at any time. Special clamping elements which fix the two adjustable parts of the middle part of the blade against each other are not necessary in this case, since the self-stoppage of the actuator is sufficient as clamping effect. Also, the guide part including the complementary screw thread can be arranged in such a way that it can take over the function of guide elements for the shifting movement at the same time.

In an advantageous further development of this instrument the guide element is held at the part carrying the projecting rim and the abutment is set at the part of the middle part fixed on the mount. With this is prevented the possibility that the rod may turn itself out of the blade and jut out interferingly when the area of reach is re-adjusted.

It is favorable to protect the rod by a covering. With this the actuator of the adjustable blade is protected against dirt. This is also an advantage from the point of view of hygiene since niches for dirt deposits can be prevented by the covering.

It is furthermore of advantage for the maintenance of the instrument if the rod has a hexagon socket at its mount end. With this a gliding off of the tool necessary for the adjustment of the blade when adjusting the area of reach of the blade is prevented.

Of necessity the middle part is secured against turning with regard to the mount by means of a rod.

The following description of two preferred design forms of the invention serves for a closer exposition in connection with the figures.

FIG. 4 shows a sectional view through another design form of the blade according to the invention along line 4—4 in FIG. 6.

FIG. 5 shows a top view of the blade of FIG. 4.

FIG. 6 shows a frontal view of the blade of FIG. 4.

FIG. 7 shows a sectional view along line 7—7 in FIG. 5 and

FIG. 8 shows two longitudinally adjustable blades set into the wound.

In the figure two blades 1 and 20 are represented which each consist of two parts, namely a fastening part 2 and 22 and an edge part 3 and 23.

Figure 1:
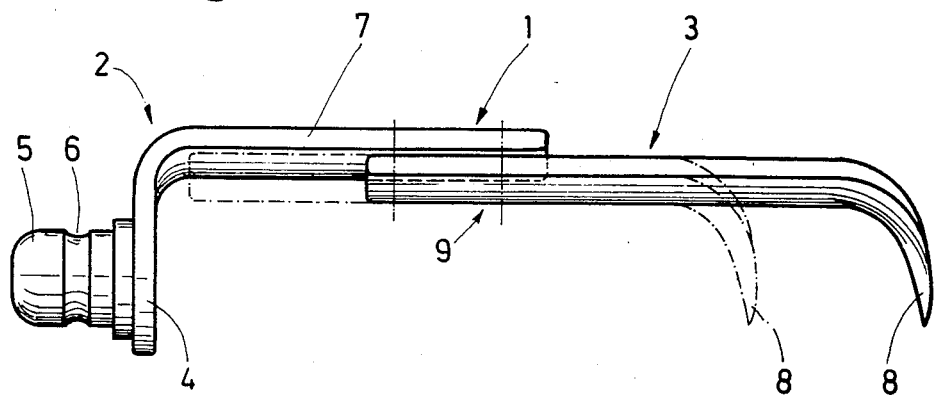
FIG. 1 shows a side view of a longitudinally adjustable blade.
Figure 2:
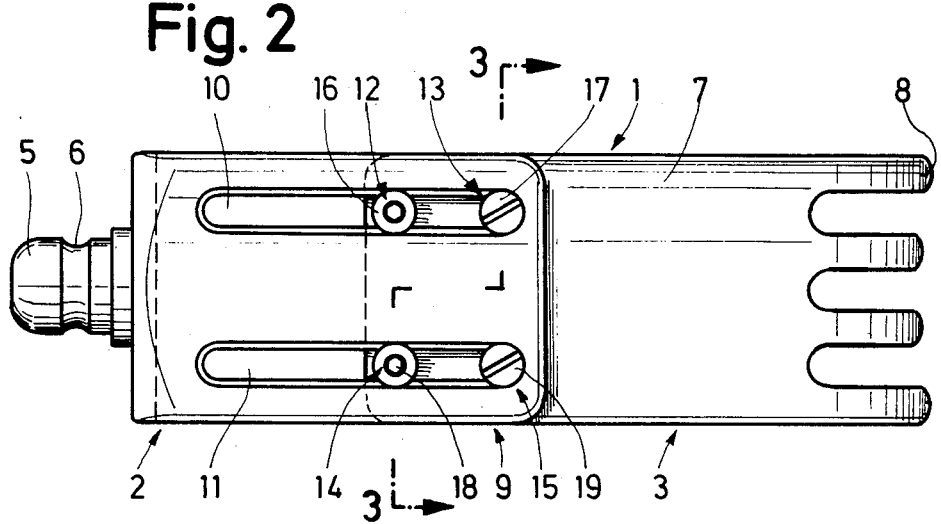
FIG. 2 shows a top view of the blade of FIG. 1.
Figure 3:
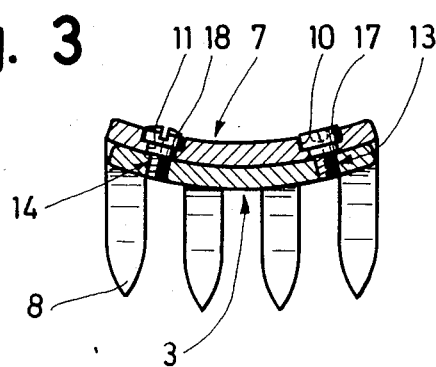
FIG. 3 shows a sectional view along line 3—3 in FIG. 2.

In the blade shown in FIGS. 1 to 3 the fastening part 2 consists essentially of a plate which is curved in an L shape, whereby the shorter side 4 has a fastening rod 5 with a surrounding ring nut 6 at its outer perimeter. The other side 7 is concavely arched diagonally to its longitudinal direction, seen from the outer side, in contrast to the first side 4.

The edge part 3 is also in the shape of a plate and is arched diagonally to its longitudinal direction in such a way that it lies square at the bottom side of the side 7. At the end farther away from the side 4 of the fastening part the edge part 3 runs out in the shape of an essentially right-angled curved teeth 8, which project from the edge part 3 in the same direction as the side 4 of fastening part 2.

The side 7 and the edge part 3 together form a middle part 9 of the blade 1, which connects the side 4 serving as fastening means and the bent-off teeth 8 to one another.

In the side 7 of the middle part two longitudinal slits 10 and 11 are set which are parallel to the blade length direction which expand step-wise on the upper side of the blade. From above four screws 12, 13, 14 and 15 are inserted into these longitudinal slits 10 and 11, whose heads 16, 17, 18 and 19 are inserted into the step-wise expanded area of the longitudinal slits 10 and 11. These screws are screwed into the edge part 3 lying squarely against the side 7. In this way they form guide elements for a relative shifting of the edge part and the fastening part. By means of these screws the two parts set movably against each other can be clamped to each other, so that a desired relative position of the two parts can be fixed. FIG. 1 shows two possible settings of the edge part as against the fastening part; in the position shown in dotted lines the spacing of the teeth 8 to the fastening side 4 is small, in the position shown with unbroken lines it is however large. All spacings inbetween can also be set.

The second design form of the blade 20 according to the invention shown in FIGS. 4 to 8 has a fastening part 22 which basically consists of a plate which is bent in an L shape in longitudinal direction, whereby a shorter side 24 has a fastening rod 5 with a surrounding ring nut 6 at its outer side. If a turning capacity of the blade 20 with reference to the mount holding it is not desired, then one must provide a rod 42, which is inserted into a complementary pocket hole in the mount, adjacent to the fastening rod 5 at the shorter side 24. The other side 27 has bent areas that are U-shaped at both longitudinal edges which serve as guide elements 44 for the edge part 23, in contrast to the first side 24 (see FIG. 7).

The edge part 23 is in the shape of a simple plate and has essentially right-angled bent-off teeth 8 at its end furthest away from the side 24 of the fastening part 22, which project from the edge part 23 in the same direction as the side 24 from the fastening part 22.

The side 27 and the edge part 23 basically form a middle part 29 of the blade 20, which connects the side 24 which serves for fastening and the bent-off teeth 8 with one another.

The edge part 23 is guided by the guide elements of the fastening part 22 in such a way that it lies squarely against the bottom side of the side 27. A further guiding is provided for the edge part 23 via a part 34, which is placed on the inside of the edge part 23 in the form of a half cylinder and is fitted into an interspace between longitudinal corners 45 of the guide elements 44. The part 34 runs in longitudinal direction up to the teeth 8 of the edge part and serves at the same time as covering 38 for the rod 30.

The part 34 has a bore hole 46 with screw threads parallel to the longitudinal direction, into which a rod 30 with a complementary screw thread section 36 can be screwed in. The rod 30 is held also at the side 24 by way of an abutment 32. At its mount end the rod 30 has a head part 48 which is provided with a hexagon socket 40.

The abutment 32 is formed at the mount side by a catch 31 in the side 24 for the head part 48 and on the opposite side by a ring nut 33 at the rod 30 with a spring ring 35 going into the nut, which lies at the surface of the side 24 that faces away from the mount.

The rod 30 is held in by the abutment in its position with reference to the side 24 in such a way that a shifting of the edge part 23 against the fastening part 22 can only be achieved by means of a turning of the rod 30. The function of the abutment 32 is to hold in the rod 30 in the fastening part 22 and to receive the axial forces acting on the rod 30 during adjustment of the area of reach. An area of reach of the blade once set can therefore not be accidentally changed. The construction of the abutment is of course not limited to the above given solution, but can be carried out in any other way known to the expert. By means of the turning of the rod 30 the screw thread 36 are screwed into the complementary screw threads of the bore hole 46 or are screwed out of them, whereby a movement of the edge part relative to the fastening part 22 is forced by the fixing in of the rod 30 in the abutment 32, with which the longitudinal expansion of the blade and with that its area of reach can be adjusted.

FIG. 8 shows blades 20 placed into a wound which lie closely against the wound edges 50. The dotted representations of the edge parts 23 as well as the double arrows show the adjustment possibilities of the blade lengths to the depth of the tissue 52 that is to be held. With the help of the blades the operation wound can be opened so far that an access to the operation area is made, shown by another arrow.

FIG. 8 above all makes clear the ease of adjustment of the longitudinal expansion of the blade in blades that are already placed into the wound, if this can be carried out outside of the operation wound. Since the actual depth of the operation wound can only be determined in an opened operation field and already inserted blades, the adjustability of blades already inserted into the wound is of special interest.

The blades shown in the figure can be inserted into a holding fixture in a mount not shown in the figure by way of a fastening cog, whereby a feather element goes into the nut 6 and secures the blade against being pulled out. The blade is then held to the mount while able to be turned around the longitudinal axis of the fastening rod 5.

If it is not desired that the blade turn with reference to the mount, then this can be prevented by using the rod 42 which goes into the holding fixture on the mount in a complementary recess.

By using blades that are longitudinally adjustable it is no longer necessary to have available a set of blades of different lengths for different blade lengths, but the desired setting can be set at any time, in that the screws connecting the two parts of the blade are released and are then tightened again after the two parts are shifted into their relative position, that is in that the rod with its screw threads is screwed in or out of the complementary screw threads at the edge part. In the latter case an additional tightening of the two parts to the blade is not necessary, since the self-tightening of the screwed-in rod is sufficient for a lasting tightening. The length adjustment can be carried out in both cases during the operation as well, whereby the design form shown in FIGS. 4 to 8 offers the additional advantage that the tool 54 necessary for length adjustment can be set at the blade outside of the operation wound.

SUMMARY

In order to make possible different spacings of the wound edge from the fastening to the mount in a surgical instrument for the splaying of wound edges with at least one blade for placement on the wound edges, which each have a blade-shaped middle part and a rim projecting at right angles opposite the middle part, and with a mount on which the blade is held on the end of the middle part opposite the projecting rim, without requiring a whole set of blades of different lengths, it is recommended that the middle part comprise two parts that are adjustable to one another, of which one is held against the mount and of which the other carries the projecting rim, and that the two parts can be fixed in different relative positions to one another, so that different lengths of the middle part formed by both parts and thus different spacings of the projecting rim from the mount result.

We claim:

1. Surgical instrument for the splaying of the edges of a wound comprising at least one blade for placement on said edges having a blade shaped middle part, a rim projecting at right angles opposite the middle part, and a mount on which the blade is held at the end of the middle part opposite the projecting rim, said middle part comprising two parts which are movable against each other, of which one is held on the mount and the other carries the projecting rim, and an actuator that moves said two parts relative to each other and fixes them in different relative positions to each other so that different lengths of the middle part and these different spacings of the projecting rim result, said actuator comprising a turnable rod with a screw thread section, a guide part with a screw thread complementary to the screw threads of the rod, and an abutment, whereby the guide part and the abutment are placed at different parts of the middle part and guide and hold the rod parallel to the movement direction, said rod being turnable for adjustment of said instrument from outside of the wound.

2. Instrument according to claim 1, wherein the two parts of the middle part lie squarely against each other.

3. Instrument according to claim 1 or 2 wherein the two parts of the middle part are arched diagonally to their adjustment direction.

4. Instrument according to claim 1 wherein at least one longitudinal slit is placed in one of the two parts into which at least one guide element held at the other part projects.

5. Instrument according to claim 4, wherein the guide element is adjustable in its spacing from the other part between a clamping setting in which the two parts are tightly pressed against each other and a release setting in which the two parts are movable toward each other.

6. Instrument according to claim 5, wherein the guide element is a locking screw screwed into the other part.

7. Instrument according to claim 5 or 6, wherein two parallel longitudinal slits are placed into the one part and that two guide elements (10, 11) project into every longitudinal slit.

8. Instrument according to claim 1, wherein the guide part is held at the part carrying the projecting rim and that the abutment is placed at the part fixed on the mount of the middle part.

9. Instrument according to claim 8, wherein the rod is protected by a covering.

10. Instrument according to claim 1 wherein the rod has a hexagon socket at the end toward the mount.

11. Instrument according to claim 1 wherein the middle part is secured by a rod against turning with reference to the mount.

* * * * *